United States Patent [19]

Annino et al.

[11] 4,059,994
[45] Nov. 29, 1977

[54] PNEUMATIC CHROMATOGRAPH

[75] Inventors: Raymond Annino, Golden, N.Y.;
Robert C. Prescott, Foxboro; Edwin
L. Karas, Sharon, both of Mass.;
Richard W. Kalinoski, East
Providence, R.I.

[73] Assignee: The Foxboro Company, Foxboro, Mass.

[21] Appl. No.: 745,392

[22] Filed: Nov. 26, 1976

[51] Int. Cl.² ................................................ G01N 31/08
[52] U.S. Cl. ........................................................ 73/23.1
[58] Field of Search ................ 73/23.1, 23; 23/232 R, 23/232 C, 254 R; 137/624.14

[56] References Cited
U.S. PATENT DOCUMENTS

| | | | |
|---|---|---|---|
| 2,951,361 | 9/1960 | Fuller | 73/23.1 |
| 3,057,184 | 10/1962 | Spracklen | 73/23.1 |
| 3,086,386 | 4/1963 | Kapff | 73/23 |
| 3,779,069 | 12/1973 | Berthold | 73/23.1 |
| 3,824,838 | 7/1974 | Ohstu et al. | 73/23.1 |

Primary Examiner—Jerry W. Myracle
Assistant Examiner—Stephen A. Kreitman
Attorney, Agent, or Firm—Parmelee, Johnson, Bollinger & Bramblett

[57] ABSTRACT

An all-pneumatic process chromatograph having a pneumatically-actuated sample-injection valve, an orifice connected in the column output line to develop a pressure signal corresponding to fluid density, a pneumatic amplifier for strengthening the pressure signal, and pneumatically-operated control means for developing a periodic sample-valve actuating signal and for selecting a particular peak of interest at a controllable time following injection of the sample. The pneumatic control means includes means automatically operable to adjust the time of peak selection in response to changes in actual peak elution time. The temperature-sensitive elements of the apparatus are contained in a chamber which is heated by a source of steam heat, with the rate of heat transfer being regulated pneumatically to maintain a relatively constant temperature within the chamber.

3 Claims, 6 Drawing Figures

LOGIC VALVE ASSEMBLY FUNCTIONS:
1. SIGNAL PRESSURE AT "a" CONNECTS PORTS 1 & 2
2. SIGNAL PRESSURE AT "b" CONNECTS PORTS 3 & 4
3. SPRING AUGMENTS "a" OR "b"

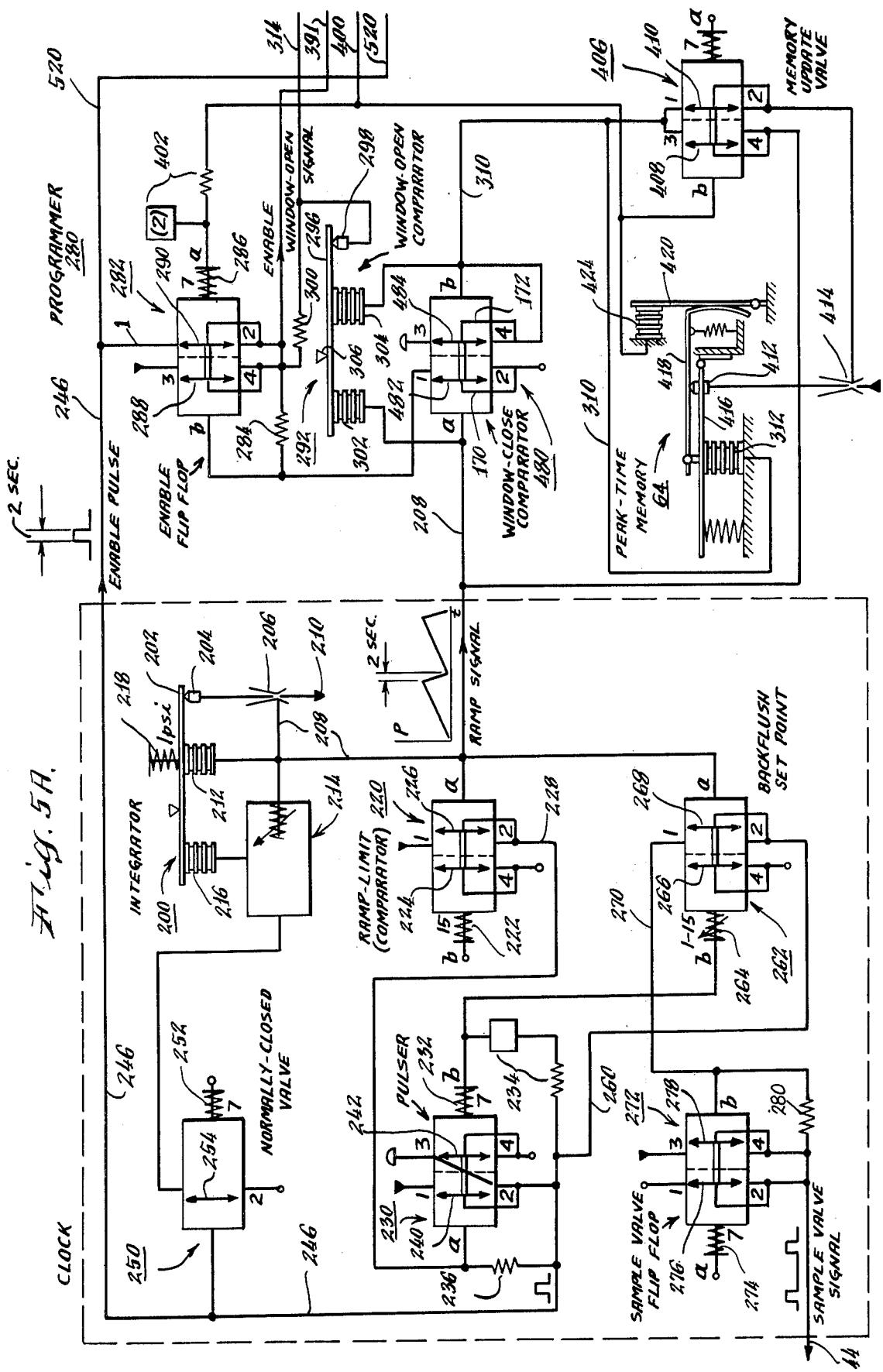

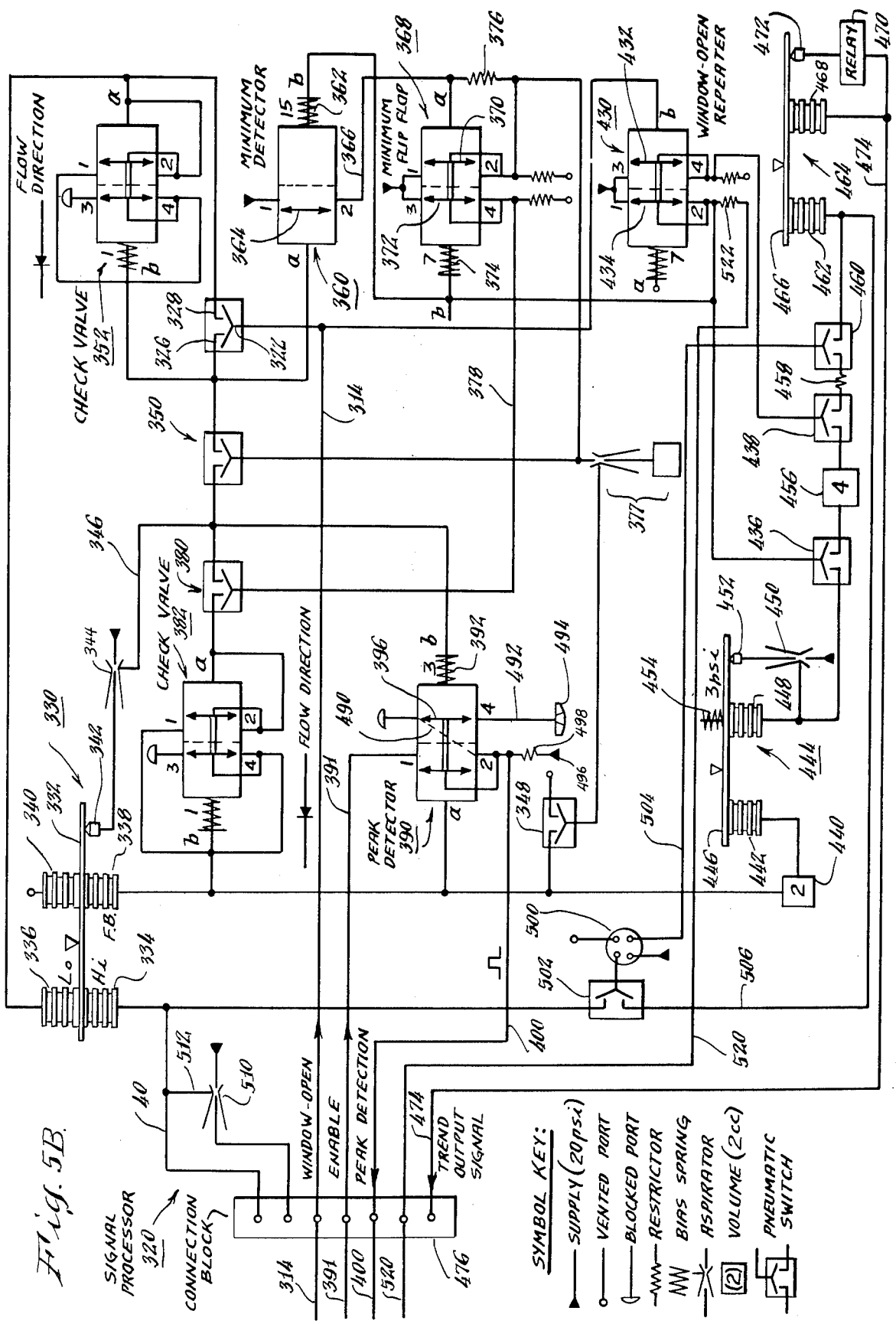

PNEUMATIC CHROMATOGRAPH

This is a division of application Ser. No. 549,930 Filed Feb. 14, 1975, now U.S. Pat. No. 4,006,624.

BACKGROUND OF THE INVENTION

1. Field of the Invention

This invention relates to chromatography, and concerns improved apparatus and techniques which in the disclosed embodiment of the invention are especially applicable to gas chromatography.

Chromatography is an analytical procedure wherein the components of a fluid mixture are physically separated to permit the individual component concentrations to be determined. In this procedure, a sample of the mixture is conducted by a carrier fluid through a column containing a material which retains the various mixture components for differing periods of time so that the components are separated to emerge at different times from the column. By providing a suitable detector at the output of the column, measurement signals are developed responsive to component concentration. Such signals typically are used to develop a so-called chromatogram comprising a series of time-separated signal peaks each having a height corresponding to the concentration of a respective component.

Although chromatographic analyzers (or "chromatographs") originally were intended for use as laboratory instruments, there has been a continuing need to provide such equipment which can be used directly with industrial processes, particularly to enhance the control of such processes. The requirements applicable to such so-called process chromatographs are however quite different from those applicable to laboratory instruments. For example, process chromatographs generally will be operated under widely varying external conditions, and must be designed to be highly reliable as well as inherently safe in operation under such conditions. In addition, chromatographs for process control should be relatively inexpensive, and must provide for simple maintenance operations whenever required.

Field conditions for a process chromatograph may often include potentially explosive atmospheres such as found in a hydrocarbon distillation plant. Thus an exposed energy source, e.g. a flame or electrical device as used in certain laboratory chromatographs, cannot be employed in a process chromatograph without costly protective equipment or enclosures because such a device can cause a violent explosion resulting in the loss of equipment and even life. The present invention provides apparatus which effectively minimizes the danger of explosion, and particularly provides a process chromatograph which can be treated is inherently safe for use in potentially hazardous atmospheres.

Process control chromatographs generally should be capable of focussing on one or two components, so as to produce concentration signals respecting such components over a series of analysis cycles in order to obtain so-called "trend" information. In accordance with another aspect of the present invention, a process chromatograph is provided which includes unique means for identifying the peak representing a particular component of interest, and for generating a measurement signal respecting only that peak during each analysis cycle. An extension of this technique makes it possible to "track" more than one component if desired.

DESCRIPTION OF THE PRIOR ART

Commercially-available chromatographs typically include: (1) an electrically-heated, temperature-controlled oven to maintain the analysis equipment and fluids being analyzed at a closely-regulated temperature, (2) a thermal-conductivity or flame-ionization detector to produce measurement signals representing component concentration, and (3) electronic programming and signal processing circuitry. All such equipment generally is divided among two housings, one of which typically requires costly explosion-proof features. U.S. Pat. No. 3,429,176, issued on Feb. 25, 1969, to William H. Topham discloses a design that is intended to minimize the requirements of the explosion-proof housing. This design nevertheless utilizes potentially dangerous sources of ignition (i.e. electrical connections), and an electric heater which requires power lines leading into the field. Even though this design conceivably might be safe during normal operation of the chromatograph, it is not of the category referred to as "intrinsically safe". That is, it is not a design which assures that ignition cannot occur even during abnormal conditions such as failure, or over-voltage applied to the power lines, or rupture of an explosion-proof conduit.

Chromatograph detectors frequently are of the thermalconductivity type, such as the hot-wire detector shown in the patent referenced above. In that type of detector, a sensor is heated electrically in a controlled fashion. The sample component is brought into contact with the sensor after emerging from the column, and alters the electrical characteristics of the heated sensor in a manner proportional to concentration. This alteration is detected electronically to develop corresponding measurement signals, typically sample peaks. The peak can be produced, for example by developing a signal corresponding to the power required to maintain a constant temperature at the sensor. Another commonly-used detector uses the flameionization technique in which the sample component is burned in the presence of another gas. The sample peaks are developed by applying an electrical potential across the flame and measuring the change in ionization rate when a particular component is eluted. Although the open flame is a potentially dangerous source of ignition, flame-proof flame-ionization detectors have been designed which reduce the danger. For example, an explosion-proof metal body can be employed as shown in U.S. Pat. No. 3,340,013. A more recent innovation is the use of an alumina body for flame-proofing and corrosion resistance. Whether such designs are entirely safe may be a matter for conjecture, but in any event it is clear that such designs are complex and relatively costly.

Both thermal-conductivity and flame-ionization detectors require electrical connections and sources of electrical power. In addition, the thermal conductivity detector is sensitive to variations in temperature. The conventional chromatographic column also is temperature-sensitive, and the combination of either of the above known detectors with the column requires highly precise temperature control, e.g. to within ±0.1° F. Such close temperature control normally has been considered to require an automatically regulated electrical heat source arranged to maintain an oven at an elevated temperature. The electrical heaters and electrical temperature control system associated with such ovens are another potentially dangerous source of ignition.

Various techniques have been developed for selecting one (or two) peak(s) of interest from among a series of successive peaks, to provide an output signal respecting only the desired peak(s). One advantageous technique is described in U.S. Pat. No. 3,717,028 (Annino et al.). However, for some applications an alternative approach to the problem is needed, and that is one of the objects of this invention.

Presently available chromatographs also present problems of reliability in operation, as well as in servicing the equipment, and it is still another object of the present invention to provide apparatus which affords significant improvements in that respect.

SUMMARY OF THE INVENTION

In one embodiment of the invention, to be described hereinbelow in detail, a process control gas chromatograph is provided that avoids the limitations and difficulties associated with conventional chromatograph designs. This new design functions entirely from fluid power sources. Thus the equipment comprises pneumatic or fluid-flow-powered operating means for carrying out all of the functions associated with the chromatograph, and pneumatically-energized control means including timing means to produce signals for coordinating the functioning of the operating means. The equipment may further include pneumatically-operated heating means to maintain the operating temperature within a suitable range of temperatures.

In one preferred embodiment, the pneumatic operating means includes a pressure-actuated sample valve for injecting the sample into the carrier, and a fluid-responsive pneumatic detector for producing a pressure signal corresponding to component concentration. The column and associated elements are located in an insulated housing which is heated from a steam heat source, with the heat transfer being pneumatically controlled to hold the temperature within a suitable range. Pneumatic logic elements also are provided in the preferred embodiment for developing timing and control signals for actuating the sample valve and repeatably selecting a component peak (or peaks) in order to develop during each analysis cycle a corresponding pneumatic signal related to the concentration of the component (or components) of interest. All of these functions are performed by energy supplied solely from (1) benevolent fluid pressure sources and (2) the flowing carrier gas. Thus, there is no need for the hazardous introduction of electrical or flame energy into the environment of the chromatograph.

BRIEF DESCRIPTION OF THE DRAWINGS

FIGS. 5A and 5B together show, in schematic symbolic format, details of the pneumatic control means used in the disclosed system.

DETAILED DESCRIPTION OF A PREFERRED EMBODIMENT

Figure 1:
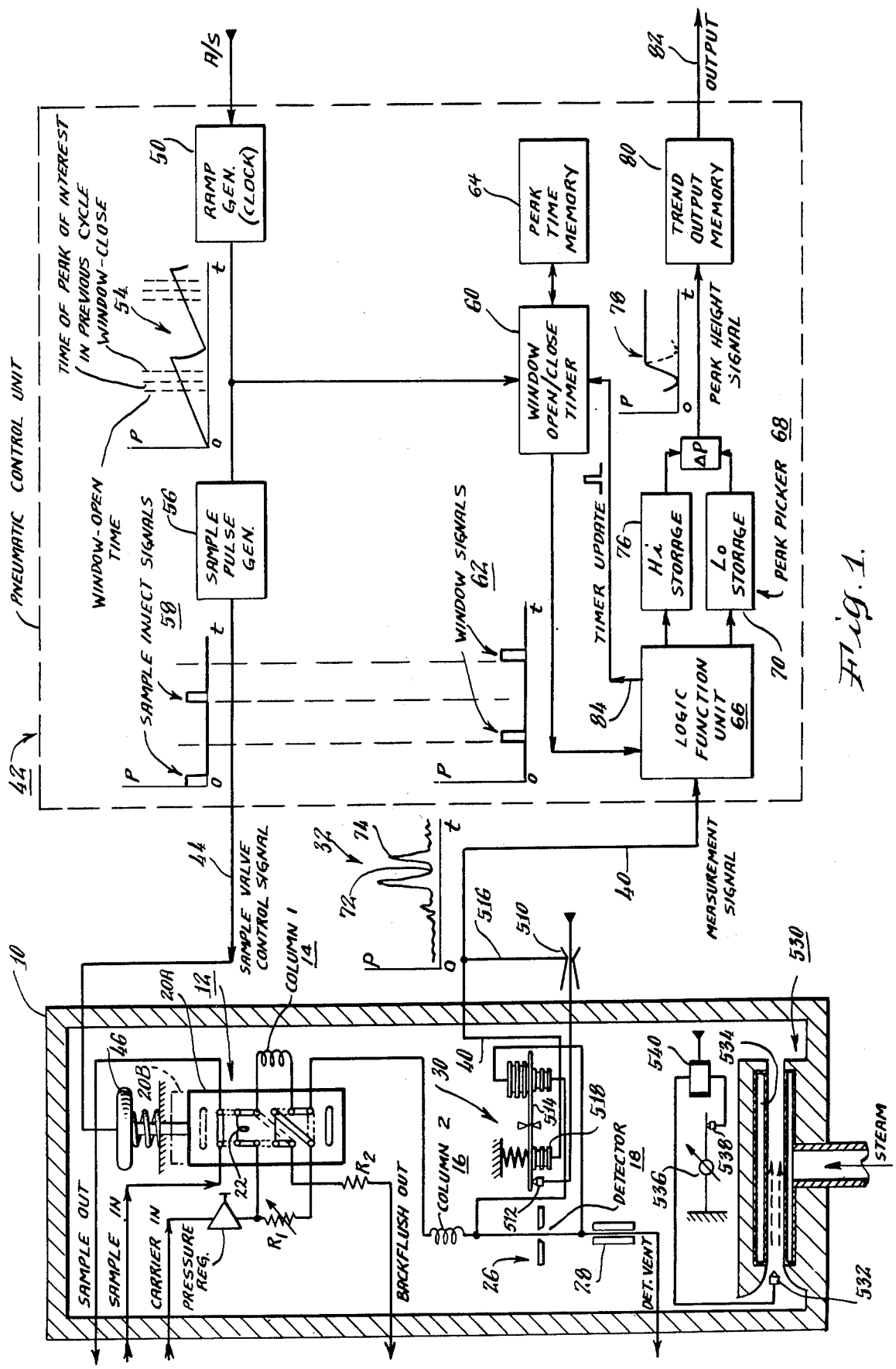
FIG. 1 is a schematic block diagram of a pneumatic chromatographic system in accordance with this invention.

Referring now to FIG. 1, there is shown a process chromatograph comprising an insulated cabinet 10 adapted for field mounting and containing the basic all-pneumatic operating elements. These elements include a sample injection valve 12 arranged to receive continuous streams of sample fluid and carrier gas, a pair of serially-connected columns 14, 16 coupled to the sample valve, and a component concentration detector 18 arranged to receive the separated components as they elute from the column 16.

The sample valve 12 may be constructed in accordance with the teachings of U.S. Pat. No. 3,748,833. As shown in that patent, the valve comprises a pair of rectangular, flat ceramic parts 20A, 20B defining a series of interconnected flow-conduits and arranged for relative sliding movement (parallel to the plane of the drawing sheet) between (1) a sample-inject position shown in solid outline, and (2) a fill/backflush position shown in interrupted outline. When in the fill/backflush position, a flow of sample fluid from the process is conducted by the valve conduits through a sample volume 22 of predetermined volume, e.g. 1 cc. When the valve is shifted to its inject position, the sample in the volume 22 is conducted by the flow of the carrier gas (typically helium) into and through the columns 14, 16 which act to separate the sample components along the path of movement, so that the individual concentrations can be measured by the detector 18.

The detector 18 includes an orifice 26 adapted to produce a pneumatic pressure signal proportional to the density (i.e. concentration) of the eluting components. This detector preferably includes flow-rate compensation means in the form of a series-connected capillary 28, the functioning of which is described in detail in copending application Ser. No. 549,929 filed by Edwin L. Karas, et al. on Feb. 14, 1975, now U.S. Pat. No. 4,033,171. The detector also includes a pneumatic amplifier 30, as described in said copending application, and which produces a relatively high-level pneumatic output signal representing by successive signal peaks (such as illustrated at 32) the measured concentrations of separated components of the sample fluid.

The pneumatic measurement signal 32 is conducted through a line 40 to an all-pneumatic control unit generally indicated at 42. This unit includes means to process the signal, as will be explained, so as to select one particular peak of interest, and to produce a so-called trend output signal for transmission to a remote point, such as a central control room, for application to process control apparatus or the like. The control unit 42 also includes means for periodically producing a pneumatic sample-inject signal for the sample valve 12 to initiate each cycle of operation. This pneumatic sample-inject signal is directed by a line 44 to a pressure-responsive device 46 (such as the device known as a "Bellofram") which shifts the valve 12 from its fill/backflush position to inject position.

The control unit 42 includes clock timing means in the form of a pneumatic ramp generator 50 arranged to produce a pressure signal, as illustrated at 54, in the form of a sawtooth-shaped wave comprising a series of identical linear ramps. This signal is directed to a sample pulse-generator 56 which, in turn, produces the periodic sample-inject pulse signals as illustrated at 58.

One of the special functions performed by the control unit 42 is that of selecting a particular peak of interest from among the multiple peaks of the measurement signal 32. Generally speaking, the peak of interest always will occur at about the same time following sample injection, and thus the control unit 42 includes timing means arranged to open a measurement "window" shortly before the predicted time of elution of the desired peak, so that the measurement signal can be processed to produce a trend output signal extracted only from the peak of interest. However, as a practical matter the time of appearance of the peak of interest actually will vary somewhat with changing conditions, such as temperature, carrier flow, or column aging, and to assure that the correct peak is selected, the control unit 42 includes self-adaptive means arranged to adjust the timing of the measurement window so as to follow variations to elution time of that peak. It also is self-adaptive to timing changes occurring within the control unit 42 as might be caused by temperature or air supply pressure changes.

Continuing with the description, as shown in FIG. 1 the pneumatic control unit 42 includes a window open/close timer 60 which receives the ramp signal from ramp generator 50, and produces a window-open signal (illustrated at 62) when the ramp pressure has reached a value corresponding to a time (see FIG. 2) which is a predetermined period prior to the expected appearance of the peak of interest from the chromatographic column 16. This window-open signal is developed by means, to be described, arranged to compare the ramp pressure signal with a previously-stored pressure in a peak-time memory 64. This memory 64 is updated each cycle by means to be described subsequently, so that its pressure will reflect the actual time of appearance of the peak of interest during the preceding cycle.

The window-open signal 62 is directed to a logic function unit 66 forming part of a pneumatic "peak-picker" generally indicated at 68. The measurement signal 32 also is directed to logic unit 66 which, by means to be described hereinafter, stores in a "Lo" storage unit 70 a pressure corresponding to the minimum signal level 72 just prior to the peak of interest 74, and stores in a "Hi" storage unit 76 a pressure corresponding to the height of the peak of interest. These two pressures are combined differentially to produce a peak output signal 78 which is directed to a trend output memory 80 to produce the trend output signal 82. The logic function unit 66 also transmits, through a line 84 leading to the window open/close timer 60, a timer update signal pulse. This pulse occurs at the instant the top of the peak of interest is detected, and serves to store in the peak-time memory 64 a pressure from ramp signal 54 at the instant the peak top is detected so that the stored pressure always will indicate the time of occurrence of the peak during the preceding operational cycle. Thus the window timer is automatically adjusted to "track" the peak of interest if the time of elution varies for any reason.

For carrying out the various control functions, the preferred control unit 42 makes use of a number of pneumatic "logic elements" which are interconnected with each other and with other types of pneumatic devices to produce the required control signals and to perform the needed actions. Generally speaking, logic elements are devices adapted to receive one or more input signals, and to produce one or more output signals in accordance with a particular logical relationship between input and output, as pre-established by the design or arrangement of the logic element.

Logic elements can be used as the basic building block of a number of different kinds of specialized devices, including, for use in the control unit 42 described herein, flip-flops, comparators, check valves, etc. A particularly suitable logic element for purposes of the present invention is described in detail in copending application Ser. No. 550,023 filed by Robert C. Prescott et al. on Feb. 14, 1975, now abandoned. The logic element shown in that application basically consists of a stacked assemblage of mated parts which define: (1) a pair of internal chambers separated by a flexible diaphragm shiftable by the chamber fluid pressures into either of two limit positions where the diaphragm alternatively opens one or the other of a pair of valves controlling the flow of fluid through respective input/output conduits, and (2) a set of passageways for conducting fluid pressure control signals to those internal chambers to control the opening-and-closing of the two valves.

Figure 2:
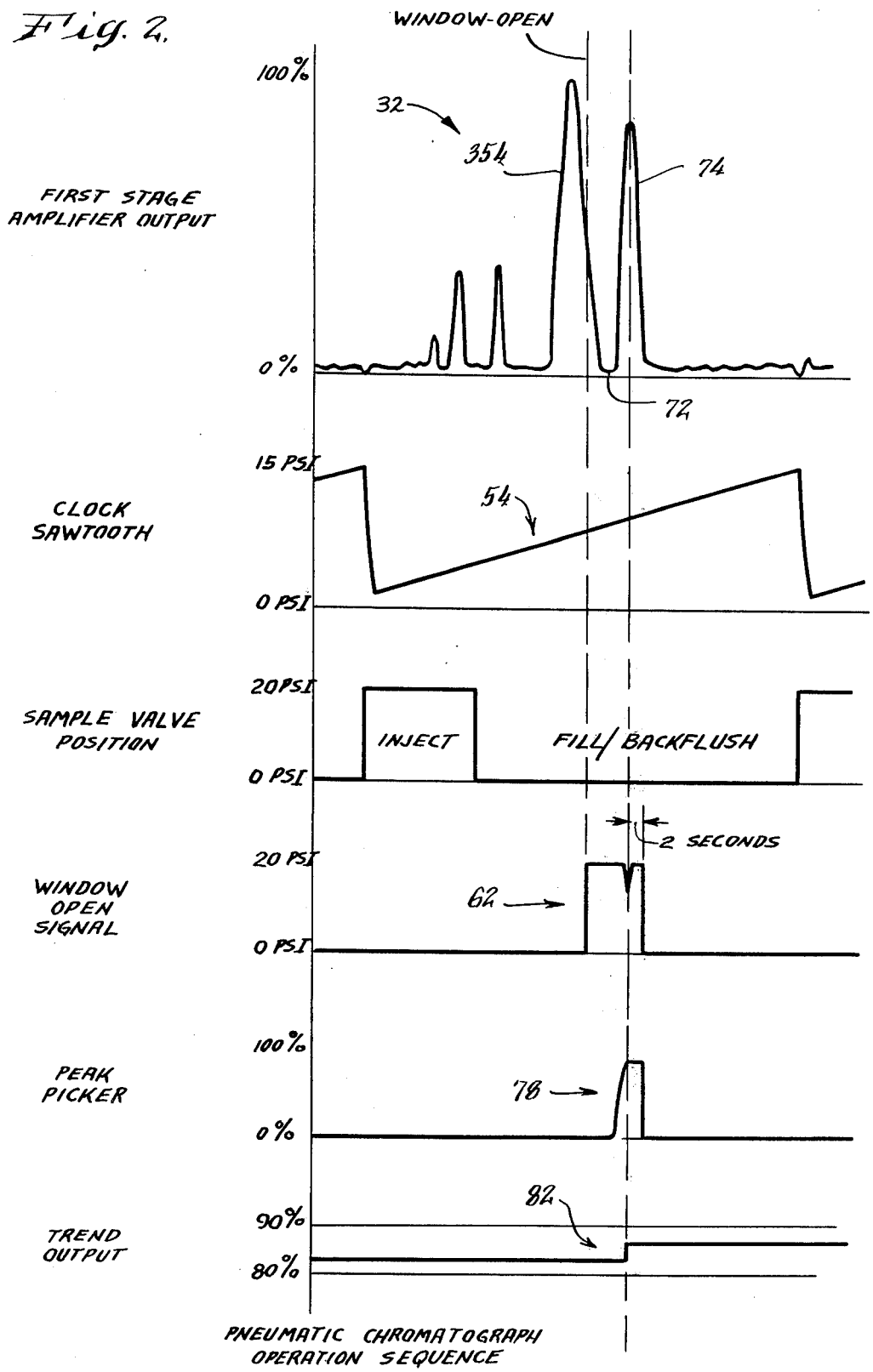
FIG. 2 presents a set of time-aligned graphs illustrating certain aspects of the system operation.
Figure 3:
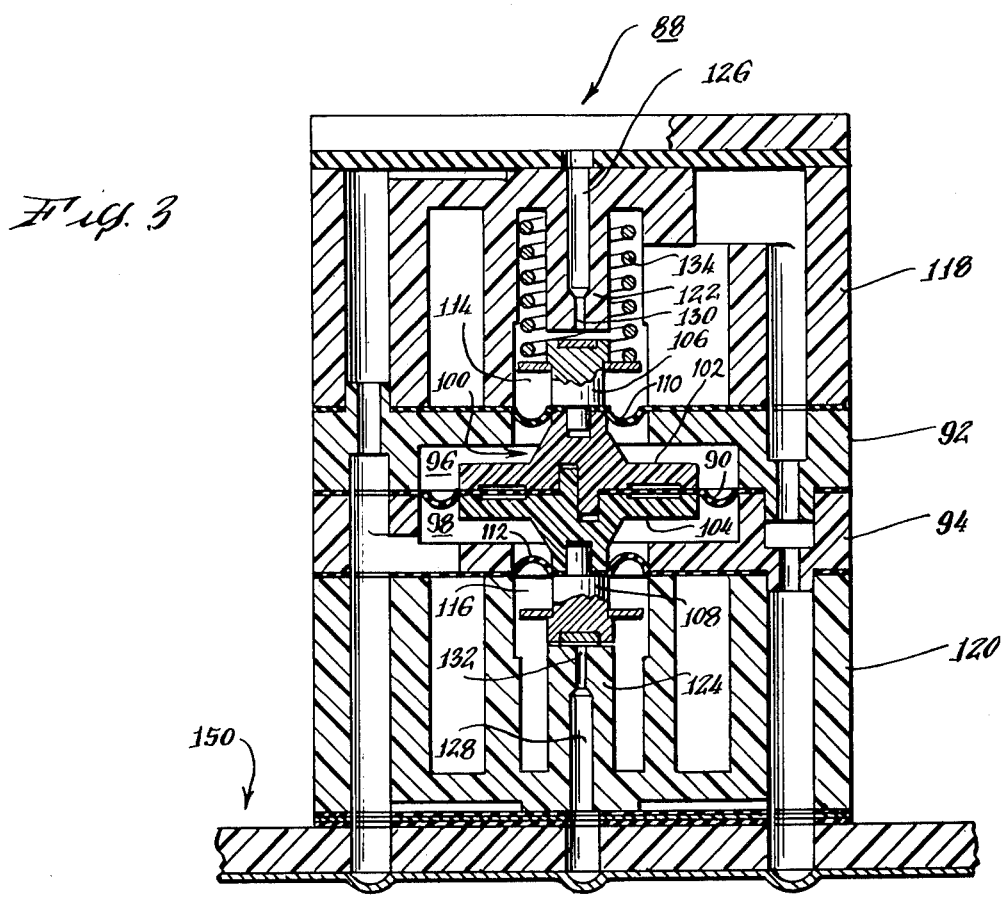
FIG. 3 is a vertical cross-section showing the construction of a logic element suited for use in carrying out the invention.

To provide an understanding of the construction of that logic element, FIG. 3 presents a cross-sectional view of the logic element identical to FIG. 2 of said copending application Ser. No. 550,023. Here it can be seen that the logic element 88 comprises a flexible central diaphragm 90 clamped securely at its periphery by a pair of identical but oppositely-facing molded-plastic spacers 92, 94. These spacers are formed internally to provide a pair of primary pressure chambers 96, 98 on opposite sides of the diaphragm 90. Signal pressures in these chambers develop corresponding forces on the diaphragm tending to move it either up or down.

The diaphragm 90 carries a coaxial valve-control structure 100 comprising a pair of identical mated plastic discs 102, 104 having raised centers the ends of which are formed with small holes to receive the corresponding mounting fingers of respective valve stems 106, 108 which are adhesively bonded in place. Each of a pair of outer flexible diaphragms 110, 112 is adhesively bonded between one valve stem and the associated plastic disc 102, 104 to seal off the respective primary chambers 96, 98 from corresponding secondary chambers 114, 116 formed in respective identical but oppositely-facing molded plastic bodies 118, 120 sealingly secured to the spacers 92, 94. These bodies are formed with interior coaxial tubes 122, 124 having internal coaxial passages 126, 128 opening out adjacent the respective valve stems 106, 108 to define a pair of valve ports 130, 132 which can be closed alternatively by valve seats at the ends of the valve stems, in a complementary fashion according to whether the diaphragm 90 is in its upper or its lower position. A bias spring 134 is provided around the upper tube 122 to tend to hold the diaphragm in its lower limit position, closing off valve port 132. This spring could be positioned about the lower tube 114 if bias of the diaphragm in the opposite direction were desired.

The coaxial passages 126, 128 and associated valve ports 130, 132 are in series with corresponding isolated input/output conduits (not shown in their entirety herein) which comprise further passageways in the logic element 88 leading to connection openings in the outer surface of the logic element. One input/output conduit includes (1) a passageway from the upper end of coaxial passage 126 to one outer connection opening, and (2) a passageway from the upper secondary chamber 114 to another connection opening. The other input- /output conduit similarly includes (1) a passageway from the lower end of coaxial passage 128 to one outer connection opening, and (2) a passageway from the lower pressure chamber 116 to another connection opening. The logic element includes two other control passageways leading from corresponding connection openings at the bottom of the element up to the primary pressure chambers 92, 94 respectively, to provide for applying control pressure signals to the diaphragm 90.

Details of the above-mentioned passageways are set forth in said copending application Ser. No. 550,023, but to simplify the presentation of the present invention, those details are not repeated herein. Generally, those passageways lead to connection openings through the bottom surface of the logic element, to provide communication with holes through the upper layer of a two-layered pneumatic circuit board 150 on which a number of logic elements and other pneumatic devices are mounted. The lower layer of this circuit board is press-formed to provide passages between the various holes through its upper layer, in accordance with the teachings of U.S. Pat. No. 3,631,881 (Bowditch), in order to effect interconnection between the various logic elements and other pneumatic devices which are mounted and supported on the board. Thus the pneumatic circuit board 150 serves a function somewhat similar to that of a printed circuit board as used in conventional electronic equipment.

The overall pneumatic control unit 42, shown in detail in FIGS. 5A and 5B, includes a relatively large number of logic elements 88 as basically shown in FIG. 3, but arranged to perform a variety of functions. It will be evident that in a drawing presentation of the overall control unit 42 it is not practicable to show each logic element in full mechanical detail, since such a presentation not only would be cumbersome, but also would obscure the basic nature of the control unit functioning. Accordingly, for purposes of presenting details of the control unit in FIGS. 5A and 5B, a symbolic diagram has been developed and used to represent logic element 88 and its functional characteristics. The basic arrangement of this symbolic representation is set forth in FIG. 4.

Figure 4:
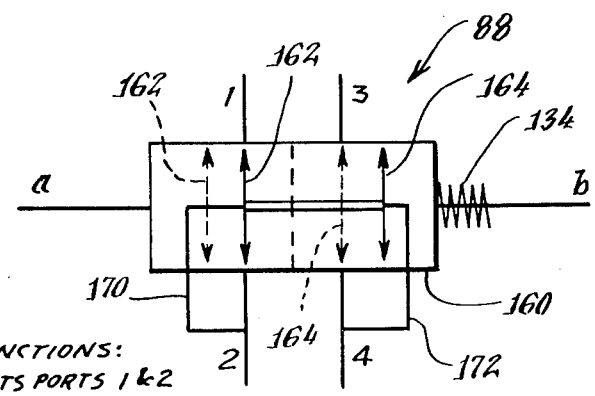
FIG. 4 is a simplified schematic diagram in symbolic format illustrating the nature and functioning of the logic element of FIG. 3.

Referring now to FIG. 4, the logic element 88 is represented as comprising an elongate valve body 160 to which is connected six pressure conduits identified with the reference characters a, b, 1, 2, 3 and 4. Conduits a and b correspond to internal control signal passageways of the logic element leading to the primary pressure chambers 96, 98, respectively, to apply control signal pressures to opposites sides of the diaphragm 90. Conduit 1 corresponds to the passageway which leads from a connection opening through the lower coaxial passage 128 to valve port 132, and conduit 2 corresponds to the passageway which leads from the lower secondary chamber 116 back out to another connection opening. Conduit 3 corresponds to the passageway which leads from a connection opening through the upper coaxial passage 126 to valve port 130, and conduit 4 corresponds to the passageway which leads from the upper secondary chamber 114 back out to another connection opening.

Shown in the valve body 160 are a pair of interlinked arrowed valve elements 162, 164 which correspond functionally to the valve seats carried by the valve stems 106, 108, respectively, and which are shiftable between a left-most limit position and a right-most limit position in accordance with the pressures from conduits a and b, and the force of bias spring 134. When the pressure from conduit a forces these elements to the right-hand position (shown in solid outline), the element 162 is aligned with conduits 1, 2 to indicate that a pneumatic channel is completed between those conduits; this state corresponds to the lower valve port 132 being open. When in this condition, the other element 164 is non-aligned with conduits 3, 4 to indicate that there is no passage between those conduits, i.e. that the upper valve port 130 is closed. If the pressure at b becomes sufficient to shift the elements 162, 164 to the left (dotted position), conduits 1, 2 will be disconnected (no passage), and conduits 3, 4 will be connected. Thus, it will be seen that the logic element consists, in effect, of two separate but interlinked two-way valves operable in a complementary fashion by the two input control pressures at conduits a and b.

FIG. 4 further illustrates at 170, 172 the action of the two secondary pressure chambers 114, 116 of the logic element 88. Whatever pressure is in conduit 2 or conduit 4 also appears in the corresponding chambers 116, 114. For example, if the element 162 is moved to the right by a signal at conduit a to connect a supply pressure from conduit 1 to conduit 2, that supply pressure will also enter chamber 116 to augment the force from the signal at conduit a. In effect, the secondary chambers are adapted to provide a positive feedback action, useful in certain applications. In a preferred embodiment, the effective areas of the secondary chambers was arranged to be a predetermined fraction of the effective areas of the primary pressure chambers, e.g., one-tenth of the latter. Thus the augmenting force has a magnitude which is 0.1 times the force from the principal pressure chamber, so that the total force will be 1.1 times the control pressure force, when the pressures at conduits 2 and a are equal.

Details of the Pneumatic Control Unit 42

Referring now to the left-hand portion of FIG. 5A, there is shown a set of pneumatic devices (all together labelled "Clock") which are interconnected to provide the ramp-and pulse-generating functions of the blocks 50 and 56 shown in FIG. 1. The Clock basically comprises a pneumatic integrator 200 of a type commonly used in modern-day process controllers for the purpose of developing reset action in the control signal. (The integrator 200 is not used herein for such purpose, however, as will be apparent as the description proceeds.)

The integrator 200 comprises a balanceable pivoted force-bar 202 with a control nozzle 204 connected to an aspirator 206 to produce in a line 208 a pneumatic signal proportional to the spacing between the nozzle and the forcebar. (Note: A detailed description of an aspirator of the type identified at 206 appears in U.S. Pat. No. 3,574,486, Bowditch et al, and will therefore not be repeated herein.) The aspirator 206 is supplied with air from a supply 210 (20 psi), and produces in line 208 an output pressure in the range from about 0 psi to 15 psi, depending upon the nozzle spacing. This pneumatic signal is directed to one bellows 212 to apply a corresponding counterclockwise torque to the force-bar 202.

The pneumatic signal in line 208 also is directed through an adjustable restrictor/capacity lag network 214 to another bellows 216 which applies a clockwise torque to the force-bar. A small fixed additional clockwise torque is applied to the force-bar by a bias spring 218, arranged to produce, for example, a torque corresponding to a bellows pressure of about 1 psi. This bias effect may be provided by the natural spring action of a bellows, avoiding the need for a separate spring. Bellows 216 preferably is arranged to provide a force-effectiveness which is 97% that of bellows 212 to compensate for the effect of air compressibility.

At the start of an integrating action, with the capacity volume of network 214 at atmospheric pressure (i.e. no torque from bellows 216), the 1 psi spring 218 will tend to press the force bar 202 towards the nozzle 204 and thereby raise the pressure in the first bellows 212 to 1 psi, to produce a balance of torques about the force-bar pivot point. Thereafter, as air from line 208 slowly passes through restrictor/capacity network 214 to bellows 216 to augment the spring bias torque, the pressure of bellows 212 correspondingly increases, so as to maintain the force-bar in balance. With a fixed bias torque from spring 218, this feedback action maintains a pressure differential between the bellows 212, 216 so as to maintain a constant flow of air through the network 214.

Consequently, the pressure in line 208 increases linearly from the starting pressure of 1 psi. This linear ramp is illustrated in FIG. 2, labelled "Clock Sawtooth". The adjustment of the restrictor in network 214 permits changing of the ramp time required to reach 15 psi, and can be set to provide a maximum time of about 30 minutes.

The ramp signal in line 208 is directed to one control conduit $a$ of a logic unit 220 of the type referred to above (see FIGS. 3 and 4). This logic unit is configured as a comparator 220 to detect when the ramp pressure has reached 15 psi, the chosen limit pressure. For this purpose, the logic element has at its left-hand side a bias spring 222 equivalent to 15 psi and arranged to oppose the force developed by the ramp pressure on the shiftable valve element 224, 226. When the ramp pressure reaches 15 psi, these elements shift to the left to connect supply pressure from conduit 1 to conduit 2 and thence to an output line 228, thereby producing a 20 psi "compare" signal on that line.

The compare signal on line 228 is directed to control conduit $a$ of another logic unit 230 arranged as a one-shot flip-flop, and referred to herein as a pulser. This pulser includes a 7 psi bias spring 232 at its right-hand end, and a feedback connection from conduit 2, through a restrictor/capacity lag network 234, to conduit $b$. Conduit 2 also is connected internally to conduit 3, which is sealed, and conduit 4 is vented. Conduit 2 also is connected through a restrictor 236 to conduit $a$.

The 20 psi pressure signal at conduit $b$ serves as a "set" signal for the flip-flop 230, by overcoming the spring bias 232 to shift valve elements 240, 242 to the right to connect supply pressure to output conduit 2. This pressure signal is transmitted through a lag network 234 to conduit $b$, and serves as the reset signal for the one-shot action of the flip-flop, by forcing elements 240, 242 back to the left after a short delay period. The network 234 is arranged to provide a reset delay which produces a signal pulse of about 2 seconds duration.

This 2-second pulser signal is directed through a line 246 to a normally-closed valve 250 in the form of a logic unit as previously described. Here the 2-second pulse is fed to control conduit $a$, and is opposed by a 7 psi bias spring 252. Thus, the valve element 254 is shifted to the right for 2 seconds, and then returned back to its normal position. During the 2-second open period, this valve connects the vent at conduit 2 through to conduit 1 and thence to the capacity tank of network 214. The capacity tank is emptied, returning the integrator 200 to its initial state to begin another ramp cycle.

The 2-second pulse on line 246 could be used to actuate the sample-inject valve 12 directly, but for certain purposes it is desirable to develop a separate sample-inject pulse having a relatively long and controllable duration, timed to provide a backflush function for the first column 14 of a two-column system such as illustrated at 14, 16. Thus, the 2-second pulse on line 246 is directed through a line 260 to conduit 2 of another logic unit 262, referred to as the "backflush set-point" unit. Conduit $a$ of this unit receives the ramp pressure from line 208, and the force of this pressure is opposed by a bias spring 264 which can be set anywhere between 1 and 15 psi.

At the start of the 2-second pulse on line 246, the shiftable elements 266, 268 of logic unit 262 are in their left-hand position, since the ramp pressure is at its maximum. Thus, the leading edge of the 2-second pulse passes through conduits 2 and 1 to another line 270 leading to conduit $b$ of yet another logic unit 272. This logic unit is arranged as a flip-flop, with a 7 psi bias spring 274 at the left, and is set when the pressure signal on conduit $b$ forces elements 276, 278 to their left-hand position. This connects supply pressure through conduit 3, conduit 4, and a restrictor 280, to act as a positive feedback signal at conduit $b$. The supply pressure from conduit 2 also is directed through line 44 (see also FIG. 1) to actuate the pressure-responsive device 46 which shifts the sample valve 12 into its sample inject position.

Immediately after the start of the 2-second pulse on line 260, the logic unit 262 returns to the condition shown in the drawing with the elements 266, 268 in their right-hand position, since the bias spring 264 overcomes the force of the reduced pressure of the ramp signal on line 210. Ultimately, after the end of the 2-second pulse on line 260, as the ramp pressure increases, it will reach a value where it overcomes the bias spring force (depending upon the spring value), and forces the elements 266, 268 to the left. When that shift occurs conduits 1, 2 connect line 260 (now vented) through line 270 to conduit $b$ of flip-flop 272. This provides a reset signal to that flip-flop, venting conduit $b$ to permit the bias spring 274 to return the flip-flop to its original state. In this reset state, the output pulse line 44 is vented so that the sample-inject valve 12 is returned to the fill-/backflush position by the spring-return action of the valve.

Conduit $b$ of pulser flip-flop 230 also is connected directly to conduit $b$ of logic unit 262, to couple thereto the lagged reset pressure signal. This is simply to provide a small augmenting of the force of spring 264 at that time, to assure stable operation of the logic unit 262 as the ramp pressure at line 208 drops towards its minimum value.

The 2-second pulse in line 246 serves as an "enable" pulse for a Programmer generally indicated at 280. This Programmer includes an enable flip-flop 282 basically comprising a logic unit as described hereinabove. The 2-second enable pulse is directed to conduit 1 of the logic unit which connects the pressure signal through conduit 2 and a restrictor 284 to control conduit $b$. The pressure at $b$ is sufficient to overcome the 7 psi bias spring 286, so that valve elements 288, 290 are shifted to the right. This connects supply pressure from conduit 3 to conduit 4 and thence to control conduit $b$ to hold the flip-flop in its set state after the 2-second enable pulse ends.

The enable flip-flop 282, when in its set state, provides supply pressure to a force-balance mechanism generally indicated at 292, and arranged to serve as a "window-open" comparator for producing the window-open signal 62 (FIG. 1). This mechanism is of well-known construction, and comprises a pivoted balanceable force-bar 296 having a sensing nozzle 298 connected through a restrictor 300 to conduit 4 of the flip-flop 282 which carries supply pressure when the flip-flop is set. The comparator 292 further includes a pair of bellows 302, 304 pressing up against the force-bar on opposite sides of the pivot point 306. The left-hand bellows 302 receives the ramp-pressure signal from the clock ramp-output line 208. The other bellows 304 receives a fixed pressure signal from a line 310 connected to a bellows 312 forming part of the peak-time memory device generally indicated at 64.

The pressure in bellows 312 represents, as will be explained, the ramp pressure at the time of occurrence of the peak of interest during the preceding cycle of operation. Since the successive analysis cycles the peak of interest ordinarily occurs at approximately the same time after sample injection, the pressure stored in bellows 312 represents the magnitude of the ramp pressure at the time the peak of interest is expected to appear.

The window-open comparator 292 is arranged to produce a "compare" signal (i.e. a "window-open" signal) when the ramp pressure in line 208 reaches a value which is 90% of the pressure stored in bellows 312. This characteristic may conveniently be achieved by setting the force-effectiveness of bellows 304 at 90% of the force-effectiveness of bellows 302, as by correspondingly fixing their relative moment arms with respect to the pivot point 206. With such an arrangement, the window-open signal occurs at a pre-selected time prior to the expected appearance of the peak of interest. This is to provide access to the detector measurement signal 32 sufficiently early to permit processing of that signal, as will be explained.

Accordingly, when the ramp pressure in comparator bellows 302 reaches 90% of the stored pressure in the other comparator bellows 304, the force-bar 296 is rotated clockwise to shut off the sensing nozzle 298, thereby cutting-off the flow of air through restrictor 300, and producing a window-open signal (20 psi) in line 314.

This window-open signal in line 314 is directed to a Signal Processor, generally indicated at 320 (FIG. 5B) where the signal is applied to the control line 322 of a pneumatic switch symbolically illustrated at 324. This switch includes input/output lines 326, 328 which are connected together internally when no pressure is applied to control line 322, but which are disconnected (valve closed) when a pressure signal (e.g. 20 psi) is applied to control line 322. Although various pneumatic devices could be used to perform such a switching function, one particularly suitable switch is described in U.S. Pat. No. 3,057,594 (Allen); a more basic disclosure of that same technology is set forth in the earlier U.S. Pat. No. 2,612,185 (Allen). The preferred embodiment of the present invention described herein makes use of a number of such devices, and for convenience each will be referred to herein as an "open/shut valve". Thus, when the window-open signal on line 314 goes high, the open/shut valve 324 is shut, or closed.

This open/shut valve 324 is connected in one pneumatic feedback path of a force-rebalance mechanism generally indicated at 330 in the upper left-hand portion of FIG. 5B. This mechanism is of known construction, comprising a pivoted force-bar 332, a Hi signal bellows 334, an opposing Lo signal bellows 336, a feedback bellows 338, and a vented spring-balance bellows 340 (provided simply to equalize the applied spring forces). The Hi bellows 334 is connected to the measurement signal line 40 to receive the detector/amplifier signal 32. A nozzle 342 senses the changes in force on the force-bar 332 due to changes in the signal pressure, and together with an aspirator 344 produces a feedback signal on line 346.

During the preliminary processing of the measurement signal 32 which appears on line 40, to be described immediately hereinafter, the feedback bellows 338 is vented through an open/shut valve 348. This is to assure that the feedback bellows during that preliminary stage of the operations does not affect the balance condition of the device 330.

Prior to the start of the window-open signal on line 314, the nozzle feedback signal in line 346 is connected through an open/shut valve 350 and the previously-mentioned open/shut valve 324 to the Lo bellows 336. Thus, the pressure in the Lo bellows tracks the measurement signal as the various peaks elute from the detector, so as to maintain the mechanism 330 in balance. When the window-open signal goes high on line 314, valve 324 closes to interrupt that feedback path, and to bring into effect an alternate feedback path through a logic unit 352 (of the type referred to above) connected in parallel with valve 324.

The logic unit 352 is arranged to provide the function of a check valve, permitting the flow of air right-to-left from conduit $a$ to conduit $b$, but not the reverse. Such a check-valve configuration is described in detail in the above-referenced copending application of Prescott et al, Ser. No. 550,023, and therefore will not be further described herein.

The window-open signal at line 314 typically occurs when the measurement signal 32 corresponds to the declining portion of the peak 354 preceding the peak of interest 74 (FIG. 2). As the signal continues to decline after window-open, the feedback path through the check-valve 352 permits the pressure in Lo bellows 336 to correspondingly decrease. However, when the minimum signal pressure 72 is reached, and thereafter the signal pressure in Hi bellows 334 starts to increase for the peak of interest 74, the check-valve 352 shuts off flow towards the Lo bellows, preventing any corresponding increase in the pressure of that bellows. Thus, the minimum signal pressure in Lo bellows 336 is locked in, and is not subject to change during the subsequent processing of the peak of interest. That Lo bellows pressure provides the base line for the subsequent peak of interest, minimizing errors from base line drift. In addition, the stored Lo bellows pressure provides a measure of any accumulated system offset errors or the like, to permit such offsets to be compensated for in the final measurement of the height of the peak of interest.

Since the feedback path to the Lo bellows 336 is closed by the check-valve 352 after the minimum signal level 72 is reached, the subsequent rise in signal pressure in Hi bellows 334 forces the force-bar 332 clockwise to tend to shut off the nozzle 342. This in turn produces a high pressure signal in line 346, signifying that the minimum signal has occurred.

This high pressure signal in line 346 is directed through open/shut valve 350 to control conduit $a$ of a logic unit 360 having a 15 psi bias spring 362 opposing the control pressure, and serving as a minimum detector. The high control pressure overcomes this bias force, and the valve element 364 is shifted to the right to connect supply pressure from conduit 1 to conduit 2 and thence to a line 366.

This supply pressure signal in line 366 is connected to conduit a of another logic unit 368 configured as a flip-flop (see the above-referenced copending application Serial No. 550,023 of Prescott et al.). The pressure at conduit a provides a set signal for the flip-flop, forcing the valve elements 370, 372 to the left against the bias spring 374. This connects supply pressure to conduit 2 and, through a feedback restrictor 376, to conduit a, thereby holding the flip-flop in its set state. The high signal on conduit 2 serves to shut the open/shut valve 350, and also is directed to an aspirator/capacity combination 377 the slightly delayed output of which shuts the valve 348 to activate the feedback bellows 338.

The other output conduit 4 of flip-flop 368 goes low at this time of minimum measurement signal 72, since the valve element 372 moves to the left to interrupt the supply pressure from conduit 3. This low signal is directed through a line 378 to another open/shut valve 380, opening that valve to make a connection from the nozzle feedback line 346 to the control conduit a of a logic unit 382 configured, like logic unit 352, as a right-to-left check valve. This check-valve connects the nozzle feedback pressure through to the feedback bellows 338 of the force-balance mechanism 330.

Accordingly, after detection of the minimum signal pressure 72, the feedback bellows 338 takes over the rebalancing function previously performed by the Lo bellows 336. The pressure in this feedback bellows will track the rising pressure of the peak of interest 74 until it reaches its highest point. At that time, the pressure in the feedback bellows will represent the height of the peak 74 with respect to the nominal base line stored in the Lo bellows 336. That is, the feedback bellows pressure represents the differential between the peak and minimum pressures.

As the peak 74 passes its maximum point, the pressure in the Hi bellows 334 decreases, and the nozzle back pressure in line 346 correspondingly starts down. However, this lowered pressure cannot be transmitted to the feedback bellows 338, due to the check-valve action of logic unit 382. Thus, the differential peak-height measurement pressure is locked in the feedback bellows 338 for subsequent processing.

The reduction in pressure in the nozzle line 346 is directed to control conduit b of a logic unit 390 configured as a comparator to provide a peak detector function. (A detailed explanation of the operation of such a comparator arrangement is given in said copending application by Prescott et al.) Control conduit a of this unit receives the pressure stored in the feedback bellows 338 for comparison with the nozzle back-pressure from line 346, the latter being augmented by a small force from a bias spring 392, e.g. 3 psi, to prevent comparator operation by any noise signals which might be on the line. When the nozzle back-pressure decreases to a level 3 psi less than the stored peak-height pressure, the comparator valve elements 394, 396 shift to the right to produce a "compare" signal signifying peak detection. This peak-detection signal is produced at conduit 2 which is connected to conduit 1 carrying the 20 psi "enable" signal pressure in line 391 from the enable flip-flop 282.

The peak detection signal from comparator 390 is directed through a line 400, and through a restrictor/capacity lag network 402, to the control conduit a of the enable flip-flop 282. This signal is augmented by the 7 psi bias spring 286, and resets the flip-flop by forcing the elements 288, 290 to the left, to disconnect supply pressure from the opposite control conduit b. Thus, after 1 or 2 seconds delay due to network 402, the enable output pressure from conduit 4 goes low. Thus the peak-detection signal on line 400 will be a pulse of 1 or 2 seconds duration.

The peak detection pulse in line 400 also is directed to the peak-time memory 64 and its associated memory update valve comprising a logic unit 406 such as described above. Prior to peak detection, the internal elements 408, 410 of this logic unit are in their left-hand position, so that conduits 1, 2 connect the pressure from a nozzle 412 and aspirator 414 to line 310 and thence to bellows 312, to maintain the bellows pressure at the proper level corresponding to the time of appearance of the peak of interest during the preceding cycle.

The peak-time memory unit 64 is of known construction, details of which are given in U.S. Pat. No. 3,525,351 (Bowditch). To simplify the presentation of this invention, the memory unit has been shown in FIG. 5A in schematic format. The device comprises a pair of pivotally-mounted arms 416, 418 arranged for movement together in parallel relationship. The upper arm 418 is associated with the nozzle 412 and, during a so-called "transmit" mode of operation, thereby controls the pressure in the bellows 312 so that it corresponds to the angular position of the arms.

In the application of the memory device 64 to the present invention, the arm 418 is normally held locked firmly in position by a leaf spring 420, so that the pressure in bellows 312, and in line 310, remains fixed at a value corresponding to the locked angular position of the arm 418.

The memory device 64 is converted into its so-called "receive" mode by releasing the pressure of the leaf spring 420 on the arm 418 to free that arm for movement with arm 416, and by connecting bellows 312 to a source of pressure which the memory device is to remember. In this mode of operation, the bellows 312 adjusts the angular position of the arms 416, 418 in correspondence to the received pressure, so that when the device is returned to its transmit mode, the output pressure from the nozzle 412 will correspond to the new position of the arms 418.

The peak-detection pulse from line 400 is directed to an arm-release bellows 424 which pushes the leaf spring 420 away from engagement with arm 418, thereby freeing that arm for movement with any changes in pressure in the memory bellows 312. At the same time, the peak detection pulse operates the memory update valve 406 to connect the memory bellows 312 to the line 208 carrying the ramp pressure signal previously described. Therefore, at peak detection, the memory bellows 312 is pressurized at a level corresponding to the time of appearance of the peak. If that time of appearance is different from the time during the previous cycle, the ramp pressure will differ from that previously stored, and that different ramp pressure will be stored in the memory bellows 312. Simultaneously, the bellows 312 will reposition the arms 416, 418 to correspond to such new pressure level. Thus, when the memory device is returned to its transmit mode, its stored pressure and its output pressure on line 310 will correspond to the new position of arms 416, 418 in accordance with the new ramp pressure picked off at the time of peak detection.

Returning now to FIG. 5B, the window-open signal in line 314 is applied not only to the open/shut switch 324, as previously described, but also to a window-open repeater 430 comprising a logic unit of the type referred to above, configured to provide complementary outputs at the respective conduits 2, 4. The window-open signal pressure is directed to control conduit *b* of that unit, and shifts the elements 432, 434 thereof to the left against the 7 psi bias spring. The output at conduit 2 goes low, to open an open/shut valve 436, while the output at conduit 4 goes high, to close another open/shut valve 438. These two valves are in series with the peak-height signal output line, and condition that output line for transfer of the peak-height signal, as will be explained hereinafter.

During the period following detection of the minimum signal level 72, the pressure signal applied to feedback bellows 338 also is applied through a capacity tank 440 to the input bellows 442 of a pneumatic driver amplifier 444. This amplifier is of known construction, having a pivoted force-bar 446 and a rebalance bellows 448 supplied with pressure from an aspirator 450 controlled by the usual nozzle 452. A 3 psi bias spring 454 is provided to translate the output pneumatic signal developed by aspirator 450 to the commonly-used 3 to 15 psi range. This output pressure is directed through the open/shut valve 436 (opened by the window-open repeater as explained above) to a capacity tank 456 where it is held for subsequent transfer.

When the enable flip-flop 282 is reset, about 1 or 2 seconds after peak-detection, the air supply pressure for the window-open signal in line 314 is cut off. Thus, the window-open signal goes low, and the complementary outputs 2, 4 of the window-open repeater 430 reverse states. This shuts the valve 436 and opens valve 438 to connect the peak-height pressure signal stored in the capacity tank 456 through a small restrictor 458 and a normally-open valve 460 to the input bellows 462 of a force-balance device serving as a trend repeater generally indicated at 464. This device includes a force-bar 466 and a rebalance bellows 468 driven from a conventional air-supplied pneumatic relay 470 controlled by a sensing nozzle 472. The final trend output signal is applied to an output line 474 which leads to a connection block 476 for transmittal on to any desired location.

When the complementary outputs of the window-open repeater 430 reverse state at close of the window, the high output from conduit 2 is connected to conduit *b* of minimum flip-flop 368, to reset that flip-flop, and also is directed to conduit *b* of minimum detector 360 to hold that unit in non-detect condition.

As noted above, the enable flip-flip 282 is automatically reset almost immediately after peak detection, and the corresponding enable and window-open signals go low at that time to return the various logic units and open/shut valves to their normal states. In some cases, however, the desired peak may not be present. Accordingly, to provide for such contingency, means are provided to automatically turn off the window-open signal after a preset time period, to return the equipment to its normal condition.

Reverting again to FIG. 5A, this window-close function is controlled by a window-close comparator generally indicated at 480 and comprising a logic unit of the type referred to hereinabove. The ramp pressure signal from line 208 is applied to conduit *a* of this unit, and is opposed by pressure at conduit *b* from the peak-time memory bellows 312. Conduit 2 is vented, so that the secondary pressure line 170 (see FIG. 4 herein, and descriptive material relating thereto) is disabled. Thus, the force tending to move elements 482, 484 to the right is that due only to the pressure from conduit *a*. However, conduit 4 is connected to conduit *b*, and, with conduit 3 sealed, the leftward force due to conduit *b* is augmented by a corresponding force due to the internal secondary pressure chamber to which passageway 172 is connected. As noted hereinabove, with reference to FIGS. 3 and 4, in a preferred arrangement the augmenting force is set to be one-tenth the principal force, thus providing a total force which is 1.1 times the force due to the pressure in the control conduit *b*.

With such an arrangement, the ramp pressure in line 208 must reach a value 10% greater than the pressure at conduit *b* before the logic unit 480 provides a "compare" output. When this value is reached, the valve element 482 will shift to the right to connect the vented conduit 2 to conduit 1, thereby venting the pressure at control conduit *b* in the enable flip-flop 282. This flip-flop thereupon resets to turn off the window-open signal as previously described.

The equipment also has provision for manual operation to achieve the effect of peak detection, for the purpose of initial set-up of the instrument, to select a particular peak. As shown in FIG. 5B, the peak detector unit 390 includes an internal passage 490 between conduit 2 and conduit 3, with the latter conduit sealed. Conduit 4 is connected through a line 492 to a port in a member 494. When a finger is placed over that port, it cuts off the flow of air from a supply 496 through a restrictor 498, and thereby raises the pressure at conduit 2 to supply level. This pressure increase appears to the enable flip-flop as a peak-detection signal, which thereupon resets to initiate the functions previously described.

At times it may be desirable to produce at the trend repeater 464 the entire chromatogram from the sample being analyzed, rather than just the value of the selected peak. For this purpose, a rotary pneumatic switch 500 is provided which is operable manually to vent a normally-closed open/shut valve 502, and to transmit supply pressure through a line 504 to the normally-open open/shut valve 460 previously mentioned. Thus, valve 502 opens to connect the detector measurement signal from line 40 through a line 506 to the input bellows 462 of the trend repeater 464. Simultaneously, valve 460 closes to isolate th trend repeater from the capacity tank 456 containing the previously-stored peak pressure. Thus the trend repeater 464 will provide a continuously varying output signal corresponding to the successive peaks in the signal 32 from the detector amplifier 30.

The pneumatic amplifier 30 (FIG. 1) includes an aspirator 510 connected to a sensing nozzle 512 adjacent the balanceable pivoted force-bar 514. The aspirator output line 516 provides the rebalance pressure for the amplifier bellows 518, and the rebalance pressure serves as the measurement signal 32 in line 40. The aspirator 510 with its air supply and output line 516 are repeated in FIG. 5B, at the connection block 476. That connection block also provides conduits (not shown) for furnishing air supply pressure to the various parts of the system requiring such pressure. The connection block 476 also carries a line 520 connecting the 2-second enable pulse from line 246 through a restrictor 522 to conduit 2 of the window-open repeater 430, in order to assure that the latter unit does not introduce unstable functioning into the system operation at the start of a cycle. After the enable pulse has subsided, the lower end of restrictor 522 is vented through line 246 leading back to the Clock pulser 230.

With further reference to FIG. 1, the equipment preferably includes a heater unit generally indicated at 530 to maintain the interior temperature reasonably constant. Preferably, this heater unit supplies heat from a benign fluid source, e.g. steam. Also the regulation of the temperature advantageously is effected by a pneumatic control arrangement which, as illustrated, includes a pneumatic nozzle 532 which directs a light flow of air through a heat-transfer tube 534. The rate of air flow is automatically controlled by a bimetal 536 which acts as a flapper for a sensing nozzle 538 coupled to a pneumatic relay and arranged to supply air to the nozzle 532. The air flow through the heat-transfer tube 534 is thereby automatically controlled so as to maintain a relatively constant temperature within the insulated compartment 10 containing the operating elements of the chromatograph. A detailed description of such a heater unit is set forth in copending application Ser. No. 550,159, filed by R. C. Prescott et al. on Feb. 14, 1975.

Although a preferred embodiment of the present invention has been described hereinabove in detail, this is not to be considered as necessarily limiting of the invention, it being understood that numerous changes can be made within the scope of the invention to suit the technical requirements of particular applications. For example, it is clear that the system approach disclosed herein lends itself to measurement of more than one component, through addition of a second logic control unit. Duplicating the unit described hereinabove.

We claim:

1. In industrial instrumentation apparatus of the type including a pressure line arranged to carry a pneumatic measurement signal representing a measurement such as the concentration of eluting components from a chromatographic analyzer and wherein the measurement signal passes through maximum and/or minimum values at least one of which is desired to be detected and retained for subsequent functions;

that improvement which comprises;

a force-balanceable member;

means for applying to said member a first force corresponding to said measurement signal;

feedback means to apply to said balanceable member a feedback force opposing said first force;

said feedback means including pressure storage means to receive a pneumatic feedback signal for developing said feedback force;

pneumatic sensing means adjacent said balanceable member for producing a pneumatic feedback signal responsive to changes in the force balance of said member; and pressure-transmitting means connecting said sensing means to said pressure storage means;

said pressure-transmitting means including check-valve means to allow flow of pneumatic fluid in one direction between said sensing means and said pressure storage means to provide that the feedback pressure in said pressure storage means tracks said measurement signal as said measurement signal varies towards one of said values, said check-valve means serving to prevent flow in the opposite direction between said sensing means and said pressure storage means so as to trap in said pressure storage means a pressure corresponding to said one value after the measurement varies away from said one value.

2. Apparatus as claimed in claim 1, wherein said check-valve means is operative to permit the flow of fluid from said sensing means to said pressure storage means, whereby to detect and store a measurement peak.

3. Apparatus as claimed in claim 1, including a second pressure storage means for developing a second feedback force on said balanceable member;

second check-valve means connected between said sensing means and said second pressure storage means permitting the flow of fluid in said opposite direction between said second pressure storage means and said sensing means; and means for activating one of said check-valve means prior to activation of the other check-valve means to provide for the detection and storage of a minimum signal value prior to the detection and storage of a subsequent signal peak.

* * * * *